US010285582B1

(12) United States Patent
Kavusi et al.

(10) Patent No.: US 10,285,582 B1
(45) Date of Patent: May 14, 2019

(54) EYE IMAGING METHODS AND DEVICES WITH REFLECTION REDUCTION

(71) Applicant: Verily Life Sciences LLC, Mountain View, CA (US)

(72) Inventors: Sam Kavusi, Menlo Park, CA (US); Charles M. Santori, Palo Alto, CA (US); Seung Ah Lee, San Francisco, CA (US); Scott Ettinger, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 3 days.

(21) Appl. No.: 15/710,521

(22) Filed: Sep. 20, 2017

Related U.S. Application Data

(60) Provisional application No. 62/406,571, filed on Oct. 11, 2016.

(51) Int. Cl.
| | |
|---|---|
| *A61B 3/14* | (2006.01) |
| *A61B 3/10* | (2006.01) |
| *A61B 3/02* | (2006.01) |
| *A61B 3/00* | (2006.01) |
| *A61B 3/15* | (2006.01) |

(52) U.S. Cl.
CPC .............. *A61B 3/1015* (2013.01); *A61B 3/14* (2013.01); *A61B 3/158* (2013.01)

(58) Field of Classification Search
CPC ........... A61B 3/103; A61B 3/14; A61B 3/113; A61B 3/024; A61B 3/1225; A61B 3/18; A61B 3/1015

USPC ........ 351/205–207, 209–210, 200, 221–222, 351/245–246
See application file for complete search history.

(56) References Cited

U.S. PATENT DOCUMENTS 5,886,767 A * 3/1999 Snook .................... A61B 3/107
351/211
8,915,592 B2 12/2014 Korb et al.
(Continued)

OTHER PUBLICATIONS

Tran, K. et al., "Construction of an Inexpensive, Hand-Held Fundus Camera through Modification of a Consumer "Point-and-Shoot" Camera", Investigative Ophthalmology & Visual Science, vol. 53, No. 12, Nov. 2012, 8 pages.
(Continued)

*Primary Examiner* — Dawayne Pinkney
(74) *Attorney, Agent, or Firm* — Christensen O'Connor Johnson Kindness PLLC

(57) ABSTRACT

An imaging device for imaging an eye includes an eyepiece, an illumination system, an imaging system, and a controller. The illumination system includes a light source that emits illumination light along an illumination path through the eyepiece to the eye to produce a retinal diffuse reflection and a corneal specular reflection. The imaging system includes a first camera that captures a retinal image based on the retinal diffuse reflection and a first set of optical elements, a second camera that captures a corneal specular reflection image based on the corneal specular reflection and a second set of optical elements. The first camera captures at least some residual corneal specular reflection in the retinal image. The controller subtracts the residual corneal specular reflection from the retinal image based on the corneal specular reflection image.

21 Claims, 2 Drawing Sheets

(56) References Cited

U.S. PATENT DOCUMENTS

| | | | |
|---|---|---|---|
| 2003/0208125 A1* | 11/2003 | Watkins | A61B 3/12 600/473 |
| 2011/0134436 A1* | 6/2011 | Podoleanu | A61B 3/1015 356/512 |
| 2013/0194548 A1 | 8/2013 | Francis et al. | |
| 2013/0335704 A1* | 12/2013 | Yates | A61B 3/152 351/208 |
| 2017/0270653 A1* | 9/2017 | Garnavi | G06T 7/0002 |

OTHER PUBLICATIONS

Umeyama, S. et al., "Separation of Diffuse and Specular Components of Surface Reflection by Use of Polarization and Statistical Analysis of Images", IEEE Transactions on Pattern Analysis and Machine Intelligence, vol. 26, No. 5, May 2004, 9 pages.

* cited by examiner

EYE IMAGING METHODS AND DEVICES WITH REFLECTION REDUCTION

CROSS-REFERENCE TO RELATED APPLICATION

This application claims the benefit of U.S. Provisional Application No. 62/406,571 filed on Oct. 11, 2016, the contents of which are incorporated herein by reference.

TECHNICAL FIELD

The present disclosure relates generally to the field of imaging, and more particularly, eye imaging methods and devices having reflection reduction.

BACKGROUND INFORMATION

Reflections and ghost images in many eye imaging applications affect the contrast and inhibit proper evaluation and diagnosis of different eye conditions by health care professionals. When imaging the eye, more than 2% of the illumination light is reflected by the cornea thereby generating a corneal reflection. Such reflection can happen even after careful choice of the illumination pattern and light angle. This corneal reflection can easily overwhelm the desired retinal image. Some imaging systems (e.g., fundus cameras) can be constructed and optimized so that the majority of the corneal reflection is outside of its field of view. However, these imaging systems are large, complex, and expensive. Furthermore, these systems have other disadvantages, including for example, being very sensitive to eye position and pupil diameter, having limited feedback loop speed, and having limited field of view. Accordingly, there is much room for significant advancement in eye imaging technology in order to reduce the size, complexity, and cost of such devices, such that they are affordable, reliable, and simpler to use by health care professionals.

SUMMARY

In one aspect, the present disclosure is directed to an imaging device for imaging an eye. The imaging device may include an eyepiece and an illumination system. The illumination system may include a light source that emits an illumination light. The light source may direct the illumination light along an illumination path and through the eyepiece to the eye producing a retinal diffuse reflection and a corneal specular reflection. The illumination system may also include an imaging system. The imaging device may include a first camera that captures a retinal image based on the retinal diffuse reflection and a first set of optical elements comprising at least one lens. The imaging device may also include a second camera that captures a corneal specular reflection image based on the corneal specular reflection and a second set of optical elements comprising at least one lens. The first camera may also capture at least some residual corneal specular reflection in the retinal image. The imaging device may also include a controller that subtracts the residual corneal specular reflection from the retinal image based on the corneal specular reflection image.

In another aspect, the present disclosure is directed to a method of imaging an eye with an imaging device. The method may include illuminating the eye using an illumination light producing a retinal diffuse reflection and a corneal specular reflection. The method may further include capturing a retinal image of the eye using a first camera based on the retinal diffuse reflection that includes at least some residual corneal specular reflection. The method may also include capturing a corneal specular reflection image of the eye using a second camera based on the corneal specular reflection. The method may further include subtracting the residual corneal specular reflection from the retinal image based on the corneal specular reflection image.

In another aspect, the present disclosure is directed to an imaging device for imaging an eye. The imaging device may include an eyepiece and an illumination system. The illumination system may include a light source that emits an illumination light. The light source may direct the illumination light along an illumination path and through the eyepiece to the eye producing a retinal diffuse reflection and a corneal specular reflection. The imaging device may also include an imaging system. The imaging system may include a first camera that captures a retinal image based on the retinal diffuse reflection and a first set of optical elements comprising at least one lens. The imaging system may also include a second camera that captures a corneal specular reflection image based on the corneal specular reflection and a second set of optical elements comprising at least one lens. The first camera may also capture at least some residual corneal specular reflection in the retinal image. The imaging device may also include a first beam splitter that directs the illumination light to the eyepiece, directs the retinal diffuse reflection to the first imaging device along a first imaging path, and directs a majority of the corneal specular reflection away from the first imaging path. The imaging device may further include a second beam splitter that is positioned to direct the majority of the corneal specular reflection to the second camera along a second imaging path. The imaging device may also include a controller that subtracts the residual corneal specular reflection from the retinal image based on the corneal specular reflection image.

DETAILED DESCRIPTION

Reference will now be made in detail to embodiments of the present disclosure, examples of which are illustrated in the accompanying drawings. Where possible, the same reference numbers will be used throughout the drawings to refer to the same or like parts.

Figure 1:
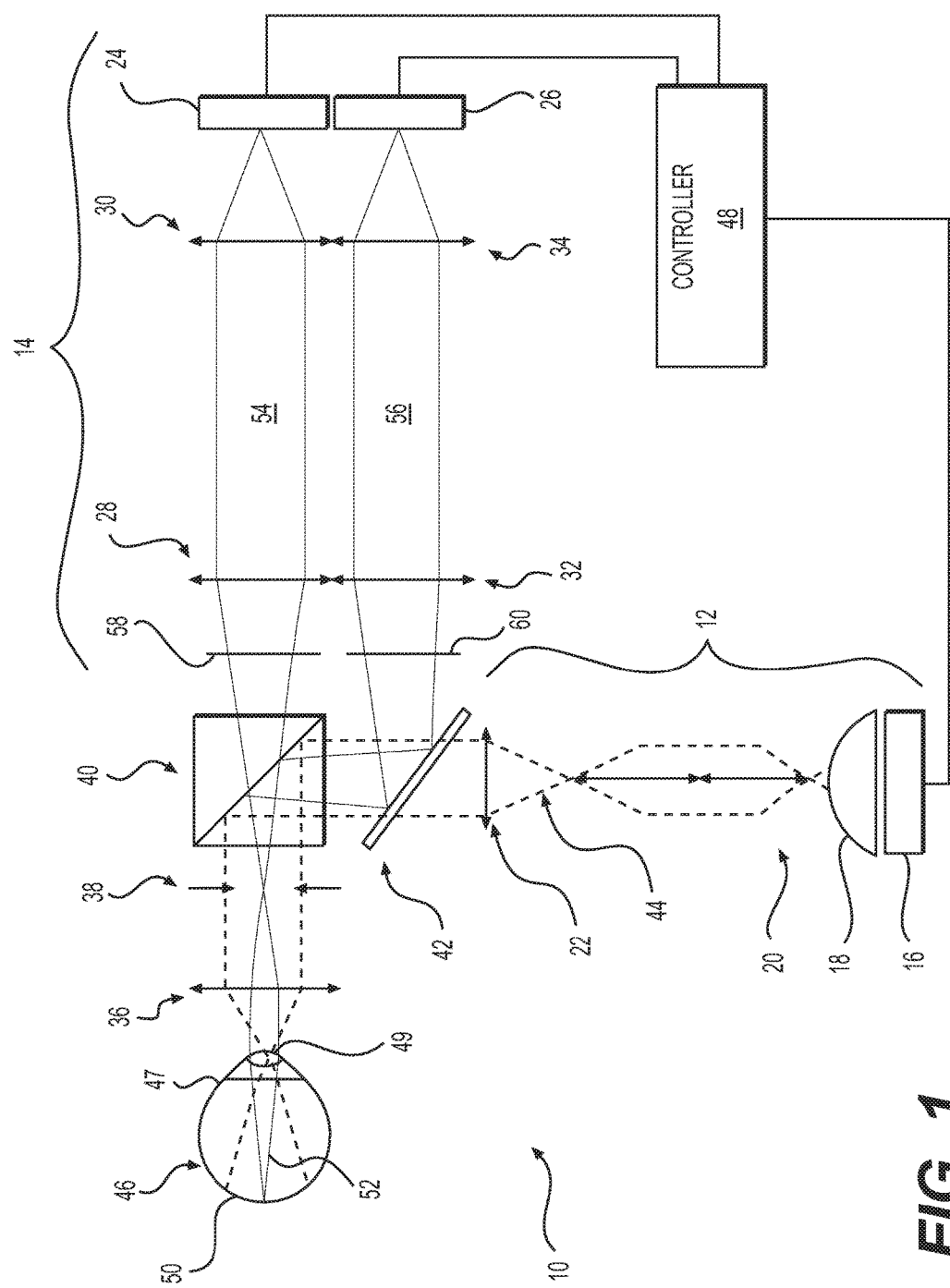
FIG. 1 is a schematic of an imaging device, according to an exemplary embodiment.

FIG. 1 is a schematic representation of an imaging device 10, according to an exemplary embodiment. In some embodiments, imaging device 10 may be an eye imaging device (e.g., a fundus camera, iris camera, or the like). In some embodiment, imaging device 10 may be configured for fluorescence imaging while in other embodiments, imaging device 10 may be configured for reflectance imaging. It is contemplated that other embodiments of the present disclosure are applicable to other suitable imaging applications besides eye imaging.

As shown in FIG. 1, imaging device 10 may include an illumination system 12 and an imaging system 14, each of which may include a plurality of components. Illumination system 12 may include a light source 16 and one or more optical elements, including, for example, a diffuser 18, annulus 20, and one or more lens (e.g., a lens 22). In some embodiments, illumination system 12 may also include a condenser. Imaging system 14 may include a first camera 24 and a first set of optical elements and a second camera 26 and a second set of optical elements. First camera 24 and second camera 26 may be any suitable type of camera or sensor (e.g., a charge-coupled device (CCD), complementary metal-oxide semiconductor (CMOS), electron-multiplied CCD (EMCCD), intensified CCD, avalanche photodiode photmultiplier tube (PMT), vidicon stacked photodiode array). The first set of optical elements may include among other things, one or more lens, for example, a first tube lens 28 and a first camera lens 30. The second set of optical elements may include among other things, one or more lens, for example, a second tube lens 32 and a second camera lens 34. Imaging device 10 may also include an eyepiece 36 and field stop 38. Eyepiece 36 may be formed of one or more lenses. Field stop 38 may determine a limiting aperture diameter and field of view and the amount of light, which reaches eyepiece 36. In some embodiments, the diameter of field stop 38 may be adjustable and/or automatically controllable. Depending on the layout, geometry, and/or application, imaging device 10 may further include a first beam splitter 40, a second beam splitter 42. Imaging device 10 may further include other optical elements, such as mirrors, additional lenses, and additional apertures (e.g., near the camera lenses 30 and 34).

Imaging device 10 may also include a controller 48 operatively connected to first camera 24, second camera 26, and light source 16. In some embodiments, controller 48 may also be operatively connected to field stop 38. Controller 48 may have a processor and one or more computer-readable medium that stores instructions or operational steps. Controller 48 may be programmed to utilize a suitable dynamic range for first camera 24 and second camera 26 based on the application. The instructions or operational steps, when executed by the processor, may operate imaging device 10, as described herein.

Illumination system 12 may be configured such that light source 16 emits an illumination light 44, which may be directed through diffuser 18, annulus 20, and one or more lenses (e.g., lens 22) to first beam splitter 40. As shown in FIG. 1, in some embodiments, illumination light 44 may pass through second beam splitter 42 in order to reach first beam splitter 40. First beam splitter 40 may be configured to direct illumination light 44 through field stop 38, eyepiece 36 toward an eye 46, which may be aligned with eyepiece 36. Illumination light 44 may pass through a cornea 47 and a pupil 49 through to a retina 50 of eye 46.

Opening pupil 49 wider is often a simple and effective way to better see the structures of the eye behind pupil 49. If desired, dilation of the pupil can be triggered with medicated eye drops (e.g., using a mydriatic agent like tropicamide) before imaging. But, eye imaging using imaging device 10 may also be done while pupil 49 is not dilated.

Illumination light 44 when it passes through cornea 47 and pupil 49 onto retina 50 may diffuse over retina 50 resulting in a retinal diffuse reflection 52 from retina 50 being directed back out of eye 46 through eyepiece 36 and field stop 38 toward first beam splitter 40. Retinal diffuse reflection 52 may pass through first beam splitter 40 and travel along a first imaging path 54 to first camera 24. First camera 24 may be configured to capture a retinal image from retinal diffuse reflection 52.

In addition to retinal diffuse reflection 52, a corneal specular reflection from illumination light 44 may get directed back toward first beam splitter 40. The corneal specular reflection may include reflected light from one or more sources. For example, the reflected light may include light reflected off the cornea (i.e., corneal reflected light) and/or other reflected light (e.g., specular reflected light).

First beam splitter 40 may be configured to reduce the corneal specular reflection that passes and travels down first imaging path 54 toward first camera 24. For example, first beam splitter 40 may divert a portion of the corneal specular reflection perpendicular to first imaging path back towards light source 16.

First beam splitter 40 may be one of a variety of different types of beam splitters. For example, when the corneal specular reflection and/or retinal diffuse reflection has a discrete spectrum having one or more discrete wavelengths or narrow spectral bands, first beam splitter 40 may be a dichroic beam splitter that selectively reflects and transmits light depending on its wavelength. For example, first beam splitter 40 may be a multiband dichroic that has multiple cut-off wavelengths and pass bands. The multiband dichroic may be selected to reflect substantially wavelengths of the corneal specular reflection and to transmit substantially wavelengths of retinal diffuse reflection 52. This configuration may be utilized, for example, when imaging device 10 is configured for fluorescence imaging.

Alternative or additionally in some embodiments, when the corneal specular reflection and/or retinal diffuse reflection 52 has a discrete spectrum, a set of corresponding notch filters or a single multi-notch filter (not shown) may be used. The notch filters or multi-notch filters may selectively reflect the discrete wavelengths or narrow spectral bands of the corneal specular reflection, thereby blocking or reducing the amount of corneal specular reflection that reaches first camera 24. Some wavelengths of retinal diffuse reflection 52 that may be the same or close to that of the corneal specular reflection may be substantially blocked by the notch filters, and thus may have substantially reduced intensity in the retinal image captured by first camera 24.

In some embodiments, when the corneal specular reflection and/or retinal diffuse reflection 52 has a continuous spectrum, first beam splitter 40 may be a long-pass dichroic beam splitter that reflects at least a portion of the wavelengths of the corneal specular reflection and transmits at least a portion of the wavelengths of retinal diffuse reflection 52.

In some embodiments, first beam splitter 40 may be a polarizing beam splitter that reflects light whose vibration orientation aligns with the transmission axis of the polarizer. When first beam splitter 40 is a polarizing beam splitter, only a portion of retinal diffuse reflection 52 may pass through first beam splitter 40 and get captured in the retinal image. For example, in some embodiments, the portion of retinal diffuse reflection 52 that is cross-polarized relative to illumination light 44 may travel down first imaging path 54 and be captured in the retinal image by first camera 24. In other embodiments, a first polarizer 58 separate from first beam splitter 40 may be positioned at any suitable location along first imaging path 54 to linearly polarize retinal diffuse reflection 52.

The portion of the corneal specular reflection that is not diverted by first beam splitter 40 (e.g., residual corneal specular reflection) may travel along first imaging path 54 toward first camera 24 and may get captured in the retinal image along with retinal diffuse reflection 52 from retina 50. In traditional imaging devices, the residual corneal specular reflection will degrade the retinal image and in some cases to such a degree that it can become increasingly difficult for health care professionals to properly evaluate the condition of the eye. In contrast, imaging device 10 can reduce or eliminate the residual corneal specular reflection from the retinal image, as is described in detail herein.

The portion of the corneal specular reflection diverted by first beam splitter 40 may be directed toward second beam splitter 42. Second beam splitter 42 may be configured to redirect the diverted corneal specular reflection from first beam splitter 40 along a second imaging path 56 to second camera 26. Second beam splitter 42 may be one of a variety of different types of beam splitters like first beam splitter 42. Thus, the description above related to first beam splitter 40 may be equally applicable to second beam splitter 40 with regard to illumination light 44 and the corneal specular reflection. In some embodiments, imaging device 10 may include a second polarizer 60 positioned at any location suitable for polarizing the corneal specular reflection. For example, second polarizer 60 may be positioned along second imaging path 56. In some embodiments, second polarizer 60 or a third polarizer (not shown) may be positioned between first beam splitter 42 and second beam splitter 40. As shown in FIG. 1, in some embodiments, first imaging path 54 and second imaging path 56 may be generally parallel.

Second camera 26 may be configured to capture a corneal specular reflection image of the corneal specular reflection from second imaging path 56, which may reveal a corneal specular reflection pattern. In some embodiments, the corneal specular reflection image may also capture other forms of specular reflected light reflected from other optical surfaces of the system or eye.

As shown in FIG. 1, controller 48 may be operatively connected to first camera 24 and second camera 26, and configured to receive and store the retinal image and the corneal specular reflection image. Based on the corneal specular reflection image, including for example, the corneal specular reflection pattern of the corneal specular reflection image, controller 48 may determine (e.g., estimate) a residual corneal specular reflection pattern of the retinal image and subtract the residual corneal specular reflection from the retinal image thus generating an improved retinal image. Because the corneal specular reflection pattern of the corneal specular reflection image changes with eye position, identifying the corneal specular reflection pattern at the same time that the retinal image is captured maximizes the accuracy of the reflection reduction. The improved retinal image may be, for example, sharper and have better contrast. The improved retinal image may decrease the difficulty of properly evaluating the condition of the eye (e.g, the fundus). The method controller 48 may use to subtract the residual corneal specular reflection from the retinal image is described in more detail further herein.

Additional functional, structural, and operational principles of various components of imaging device 10 are described in further detail below.

Light source 16 may be one or more of a variety of different types of light sources. For example, light source 16 may be a multi-color light source that emits light with one or more wavelengths. In some embodiments, the multi-color light source may have a continuous spectrum. For example, the multi-color light source may be a broadband light source, such as a supercontinuum laser, a white light source (e.g., a high-pressure mercury lamp, a xenon lamp, a halogen lamp, or a metal halide lamp), or one or more LEDs. In other embodiments, the multi-color light source may have a discrete spectrum. For example, the multi-color light source may be a combination of pulsed or continuous "single-wavelength" lasers that emit light with very narrow spectra. In some embodiments, light source 16 may be halogen lamp(s) or incandescent bulb(s).

In some embodiments, as shown in FIG. 1, light source 16 may be operatively connected to controller 48. Controller 48 may modulate the operational states of light source 16. For example, the processor may activate or deactivate light source 16, modulate the duration of a pulse if light source 16 is a pulsed light source, and/or switch or tune the emission wavelengths of light source 16. In some embodiments, light source 16 may include both visible and near-infrared (NIR) sources that can be turned on independently. For example, controller 48 may be programmed to us the NIR source for alignment and use the visible light, which may be flashed briefly to capture the retinal image and corneal specular reflection image.

In some embodiments, imaging device 10 may include and utilize diffuser 18 to evenly diffuse illumination light 44 beamed from light source 16. In some embodiment, illumination light 44 may then be focused by a series of lenses through an annular aperture, which then passes through a central aperture to form annulus 20.

As described herein, imaging device 10 may include a variety of lenses (e.g., lens 22, first tube lens 28, second tube lens 32, first camera lens 30, and second camera lens 34). The lenses may be any suitable lens type and be any suitable geometry. For example, the lenses may be camera lenses, tube lenses, singlet lenses, achromatic doublet lenses, or any other suitable type. The lens geometries may be, for example, biconvex, planoconvex, positive meniscus, negative meniscus, planoconcave, or biconcave, or other suitable geometry.

Imaging device 10 may advantageously have additional technical features and capabilities to enhance its functionality and performance. For example, in some embodiments, imaging device 10 may include a time-of-flight sensor(s) and/or a structured-light sensor(s) (not shown). The time of flight sensor can be used to measure the time of flight of a light signal between the camera and the subject for each point of the image. The structure-light sensor can be used to measure the shape of an object using projected light patterns and a camera. Controller 48 may be operatively connected to the time-of-flight sensor and/or the structured-light sensor. Controller 48 may be programmed with instructions to use either the time-of-flight sensor and/or the structure-light sensor to measure a variety of parameters, including for example, relative distances between imaging device 10 and eye 48, relative distances between parts of eye 48, corneal shape, pupil diameter, etc. In some embodiments, controller 48 may be programmed with instructions to use the corneal specular reflection image for estimating additional system and eye parameters or values. For example, controller 48 may be programmed to use the reflected image to estimate the distance or angle of eye 48 to imaging device 10 (e.g., eyepiece 36). In some embodiments, controller 48 may also be programmed to use the corneal specular reflection image and/or the retinal image to detect certain eye conditions. For example, controller 48 may be programmed to detect dry eye, cataract, or corneal abrasion. In some embodiments, detection of one or more of these conditions may further be used by controller 48 to improve the image quality of the retinal image, which may provide further valuable information for diagnostic screenings.

Controller 48 may use one or more techniques for subtracting the residual corneal specular reflection from the retinal image. One exemplary technique may use, for example, pixel by pixel subtraction of the corneal specular reflection image from the retinal image. Before the subtraction a transformation (e.g., linear) may be applied at the pixel and/or small kernel level. As described herein, controller 48 may determine a variety of relevant parameters (e.g., corneal shape, pupil size, retinal reflectivity, eye position/orientation, etc.) and these parameters may be used to define the parameters of the transformation.

The scaling applied to the corneal specular reflection image may be different for each pixel. In some embodiments, the scaling may follow a mathematical formula or may be based on a look-up table derived from calibration measurements. For embodiments where the scaling is based on a mathematical formula, the formula may be based on the polarization transformation that occurs in Fresnel reflections at nonzero incidence angles, which will affect the two paths differently and have a radial dependence. This may be implemented, for example, very similarly to a lens shading correction and may be applied at small kernels in order to avoid noise increases.

In some embodiments, before pixel subtraction, controller 48 may apply image registration between the retinal image and the corneal specular reflection image. For example, in some embodiments the retinal image may be the reference or fixed image and geometric transformation may be applied to the corneal specular reflection image so that it aligns with the retinal image (i.e., the reference image). In some embodiments, the corneal specular reflection image may be designated the reference image and geometric transformation may be applied to the retinal image so that it aligns with the corneal specular reflection image (i.e., the reference image).

In some embodiments, before pixel subtraction, controller 48 may apply one or more image processing techniques. For example, controller 48 may apply different kernel types and/or sizes to one or both of the images (i.e., the retinal image and the corneal specular reflection image). Application of the kernels can act as spatial filtering of the images.

Figure 2:
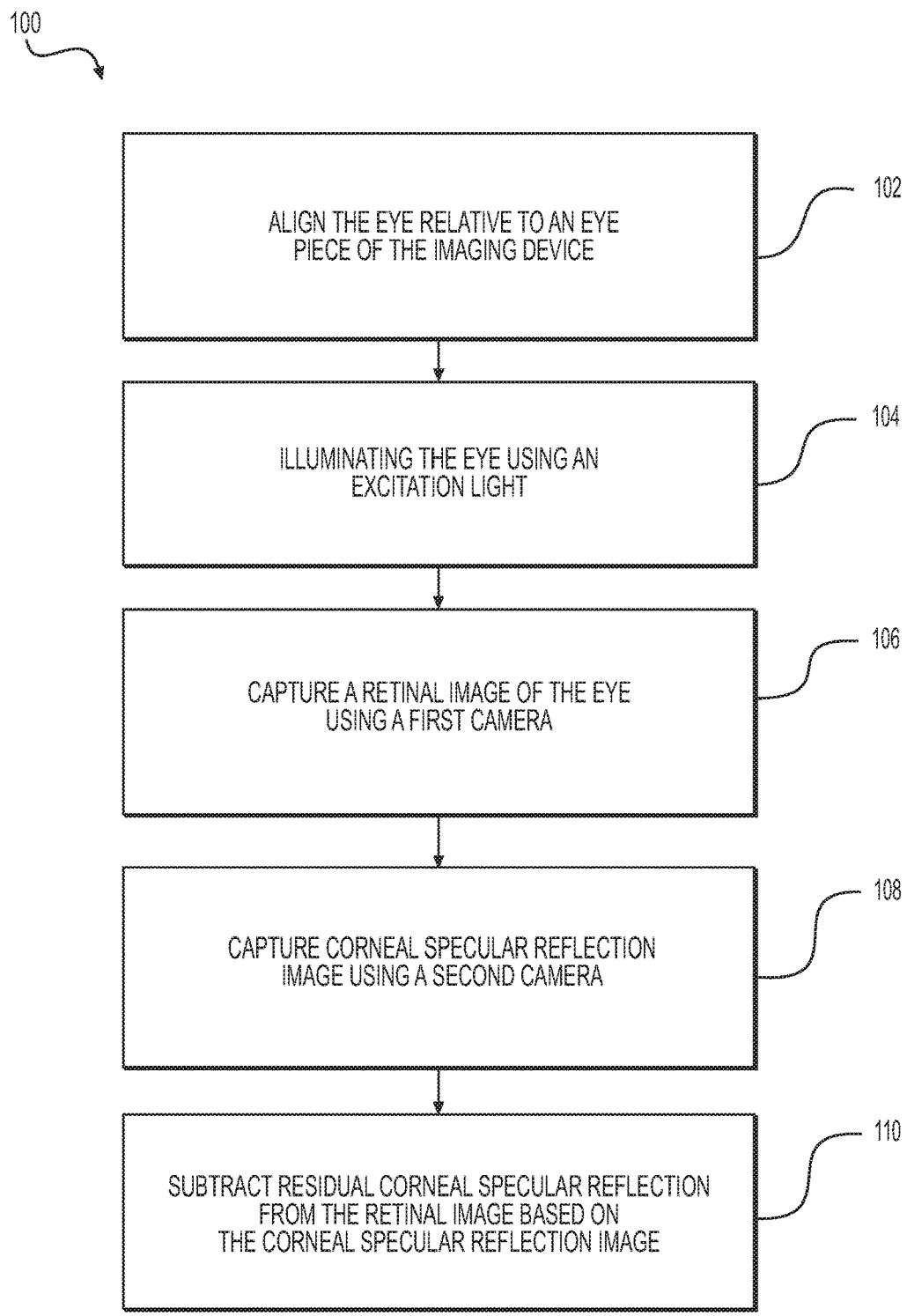
FIG. 2 is a flow chart illustrating a method of eye imaging, according to an exemplary embodiment.

Imaging device 10 as described herein may be utilized to perform a variety of methods of eye imaging. For example, a method 100 of eye imaging will be explained with reference to FIG. 2, which is a flow chart showing steps of method 100. Method 100 may begin at step 102 by aligning the eye relative to an eye piece of the imaging device. At step 104, method 100 may include illuminating the eye using an illumination light. At step 106, method 100 may include capturing a retinal image of the eye using a first camera. The retinal image may include residual corneal specular reflection captured by the first camera. At step 108, method 100 may include capturing a corneal specular reflection image using a second camera. As described herein, the corneal specular reflection image may include the corneal specular reflection. The corneal specular reflection image may be captured by the second camera at the same time the first camera is capturing the retinal image. At step 110, method 100 may include subtracting the residual corneal specular reflection from the retinal image based on the corneal specular reflection image. For example, in some embodiments the subtracting may be a pixel by pixel subtraction of the corneal specular reflection image from the retinal image.

Optionally, method 100 may also include one or more additional steps. For example, method 100 may also optionally include applying a transformation (e.g., linear) at the pixel and/or small kernel level before the subtraction. In some embodiments, method 100 may also optionally include applying scaling to the reflected image which may be different for each pixel. In some embodiments, the scaling may follow a mathematical formula or may be based on a look-up table derived from calibration measurements. In some embodiments, method 100 may also optionally include applying image registration between the retinal image and the corneal specular reflection image before the pixel subtraction.

In some embodiments, method 100 may also optionally include one or more image processing techniques, for example, applying different kernel types and/or sizes to one or both of the images (i.e., the retinal image and the corneal specular reflection image).

The foregoing description has been presented for purposes of illustration. It is not exhaustive and is not limited to precise forms or embodiments disclosed. Modifications and adaptations of the embodiments will be apparent from consideration of the specification and practice of the disclosed embodiments.

Although described in relation to use for eye imaging, it is understood that the imaging device of the present disclosure described herein may be employed for other imaging applications.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. For example, the term feces as used herein is intended to denote either the singular or plural form. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Computer programs, program modules, and code based on the written description of this specification, such as those used by the microcontrollers, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An imaging device for imaging an eye, comprising:
   an eyepiece;
   an illumination system including a light source coupled to emit illumination light along an illumination path that passes through the eyepiece to the eye to produce a retinal diffuse reflection and a corneal specular reflection;
   an imaging system including:
      a first camera coupled to capture a retinal image based on the retinal diffuse reflection;
      a first set of optical elements including at least one lens;
      a second camera coupled to capture a corneal specular reflection image based on the corneal specular reflection; and
      a second set of optical elements including at least one lens, wherein the first camera is coupled to capture at least some residual corneal specular reflection in the retinal image; and
   a controller including logic that when executed causes the controller to perform operations including:
      applying a transformation to at least one of the corneal specular reflection image or the retinal image; and
      subtracting the residual corneal specular reflection from the retinal image based on the corneal specular reflection image, wherein the subtracting includes subtracting the corneal specular reflection image from the retinal image by executing a pixel by pixel subtraction after applying the transformation.

2. The imaging device of claim 1, further comprising:
   a first beam splitter that directs the illumination light to the eyepiece, directs the retinal diffuse reflection to the first imaging device along a first imaging path, and directs at least some of the corneal specular reflection away from the first imaging path besides the at least some residual corneal specular reflection; and
   a second beam splitter that is positioned to direct at least some of the corneal specular reflection to the second camera along a second imaging path.

3. The imaging device of claim 2, wherein the first beam splitter is a polarizing beam splitter.

4. The imaging device of claim 2, wherein the first imaging path and the second imaging path are generally parallel.

5. The imaging device of claim 2, further comprising a first polarizer positioned in the first imaging path, a second polarizer positioned in the second imaging path, and a third polarizer position in the illumination path.

6. The imaging device of claim 2, wherein the illumination path is perpendicular to the first imaging path and the second imaging path and includes a polarizer.

7. The imaging device of claim 1, wherein the illumination system further comprises an annulus and at least one diffuser.

8. The imaging device of claim 1, wherein the first camera captures the retinal image and the second camera captures the corneal specular reflection image at the same time.

9. The imaging device of claim 1, further comprising at least one of a time-of-flight sensor and a structured light sensor.

10. The imaging device of claim 1, wherein the transformation is applied at a pixel level.

11. The imaging device of claim 1, wherein applying the transformation comprises scaling the corneal specular reflection image and the scaling follows a mathematical formula based on a polarization transformation that occurs in Fresnel reflections at nonzero incidence angles.

12. The imaging device of claim 1, wherein the controller includes further logic that when executed causes the controller to perform additional operations comprising:
   applying image registration between the retinal image and the corneal specular reflection image before the subtracting.

13. The imaging device of claim 1, wherein applying the transformation comprises:
   applying different kernel sizes to the corneal specular reflection image than applied to the retinal image.

14. The imaging device of claim 1, wherein applying the transformation comprises:
   generating an estimate of at least one of an eye position, an eye orientation, or a corneal radius of curvature based on the corneal specular reflection image; and
   using the estimate to improve the subtraction of the residual corneal specular reflection from the retinal image.

15. A method of imaging an eye with an imaging device, the method comprising:
   illuminating the eye using an illumination light producing a retinal diffuse reflection and a corneal specular reflection;
   capturing a retinal image of the eye using a first camera based on the retinal diffuse reflection that includes at least some residual corneal specular reflection;
   capturing a corneal specular reflection image of the eye using a second camera based on the corneal specular reflection;
   applying a transformation to at least one of the corneal specular reflection image or the retinal image; and
   subtracting the residual corneal specular reflection from the retinal image based on the corneal specular reflection image, wherein the subtracting includes subtracting the corneal specular reflection image from the retinal image by executing a pixel by pixel subtraction after applying the transformation.

16. The method of claim 15, further comprising:
   directing via a first beam splitter the illumination light to the eye, the retinal diffuse reflection to the first imaging device along a first imaging path; and the majority of the corneal specular reflection away from the first imaging path besides the residual corneal specular reflection; and
   directing via a second beam splitter the corneal specular reflection from the first beam splitter to the second camera along a second imaging path.

17. The method of claim 15, wherein the transformation is applied at a pixel level.

18. The method of claim 15, wherein applying the transformation comprises scaling the corneal specular reflection image before the subtracting, wherein the scaling follows a mathematical formula based on a polarization transformation that occurs in Fresnel reflections at nonzero incidence angles.

19. The method of claim 15, further comprising applying image registration between the retinal image and the corneal specular reflection image before the subtracting.

20. The method of claim 15, wherein applying the transformation comprises applying different kernel sizes to the corneal specular reflection image than applied to the retinal image.

21. An imaging device for imaging an eye, comprising:
   an eyepiece;
   an illumination system including a light source that emits an illumination light, wherein the light source directs the illumination light along an illumination path and through the eyepiece to the eye producing a retinal diffuse reflection and a corneal specular reflection;

an imaging system comprising:
- a first camera that captures a retinal image based on the retinal diffuse reflection;
- a first set of optical elements comprising at least one lens;
- a second camera that captures a corneal specular reflection image based on the corneal specular reflection; and
- a second set of optical elements comprising at least one lens, wherein the first camera also captures at least some residual corneal specular reflection in the retinal image;

a first beam splitter that directs the illumination light to the eyepiece, directs the retinal diffuse reflection to the first imaging device along a first imaging path, and directs at least some of the corneal specular reflection away from the first imaging path;

a second beam splitter that is positioned to direct at least some of the corneal specular reflection to the second camera along a second imaging path; and a controller including logic that when executed causes the controller to perform operations including:
- applying a transformation to at least one of the corneal specular reflection image or the retinal image; and
- subtracting the residual corneal specular reflection from the retinal image based on the corneal specular reflection image, wherein the subtracting includes subtracting the corneal specular reflection image from the retinal image by executing a pixel by pixel subtraction after applying the transformation.

* * * * *